(12) United States Patent
Thompson et al.

(10) Patent No.: US 6,287,301 B1
(45) Date of Patent: *Sep. 11, 2001

(54) CATHETER HAVING IMPROVED TORQUE TRANSMISSION CAPABILITY AND METHOD OF MAKING THE SAME

(75) Inventors: Russell B. Thompson, Los Altos; Sidney D. Fleischman, Menlo Park; James G. Whayne, Saratoga; David K. Swanson, Mountain View; Huy D. Phan, San Jose; Dennis Michael O'Brien, Mountain View, all of CA (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,833

(22) Filed: Sep. 10, 1998

Related U.S. Application Data

(63) Continuation-in-part of application No. 08/902,742, filed on Jul. 29, 1997, now abandoned.

(51) Int. Cl.$^7$ .................................................. A61B 18/04
(52) U.S. Cl. ............................................. 606/33; 604/524
(58) Field of Search ...................... 606/33, 41; 600/585; 607/116, 119, 122, 125, 126; 604/95.01, 264, 523, 524, 525

(56) References Cited

U.S. PATENT DOCUMENTS

| | | |
|---|---|---|
| 5,190,050 | 3/1993 | Nitzche . |
| 5,273,535 | 12/1993 | Edwards et al. . |
| 5,328,467 * | 7/1994 | Edwards et al. ........................ 604/95 |
| 5,397,321 | 3/1995 | Houser . |
| 5,431,168 | 7/1995 | Webster . |
| 5,545,200 * | 8/1996 | West et al. ........................... 607/122 |
| 5,555,618 | 9/1996 | Winkler . |
| 5,571,073 | 11/1996 | Castillo . |
| 5,582,609 | 12/1996 | Swanson . |
| 5,643,255 | 7/1997 | Organ . |
| 5,656,029 | 8/1997 | Imran et al. . |
| 5,662,606 | 9/1997 | Cimino et al. . |
| 5,676,653 | 10/1997 | Taylor et al. . |
| 5,685,868 | 11/1997 | Lundquist . |
| 5,772,641 | 6/1998 | Wilson . |
| 5,820,591 | 10/1998 | Thompson . |
| 5,827,278 | 10/1998 | Webster, Jr. . |
| 5,964,757 | 10/1999 | Ponzi . |
| 6,066,125 | 5/2000 | Webster, Jr. . |

FOREIGN PATENT DOCUMENTS

| | | |
|---|---|---|
| WO97/42996 | 11/1997 | (WO) . |
| WO 99/06095 | 2/1999 | (WO) . |
| WO 99/30410 | 6/1999 | (WO) . |

OTHER PUBLICATIONS

PCT Search Report for Int. Appl. No. PCT/US98/15163.

* cited by examiner

Primary Examiner—John P. Leubecker
Assistant Examiner—R Kearney
(74) Attorney, Agent, or Firm—Henricks, Slavin & Holmes LLP

(57) ABSTRACT

A catheter having improved steering and torque transmission capabilities.

44 Claims, 13 Drawing Sheets

FIG. 8     FIG. 9
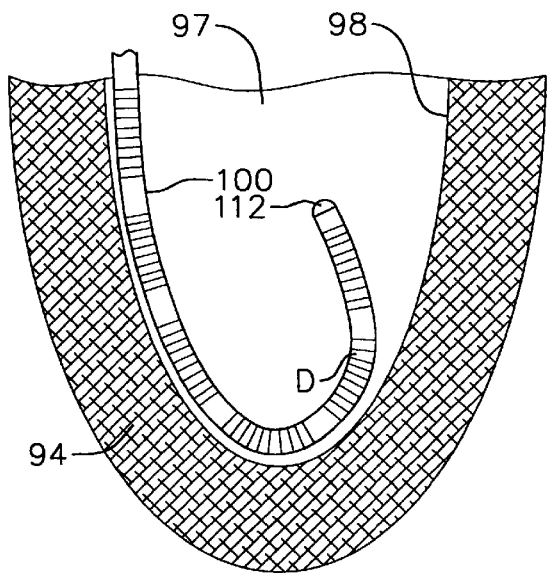
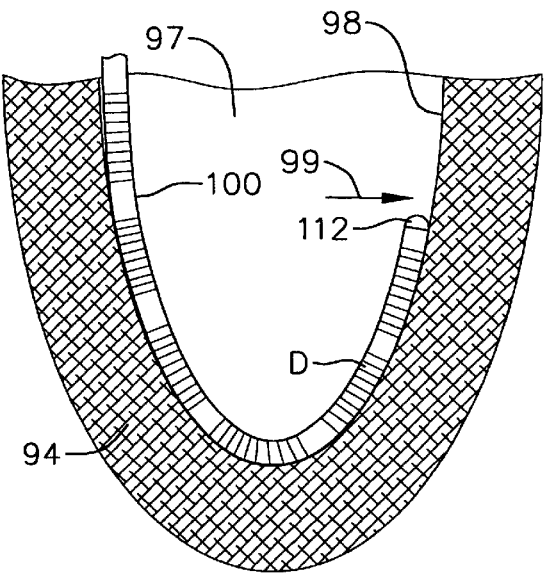
FIG. 10
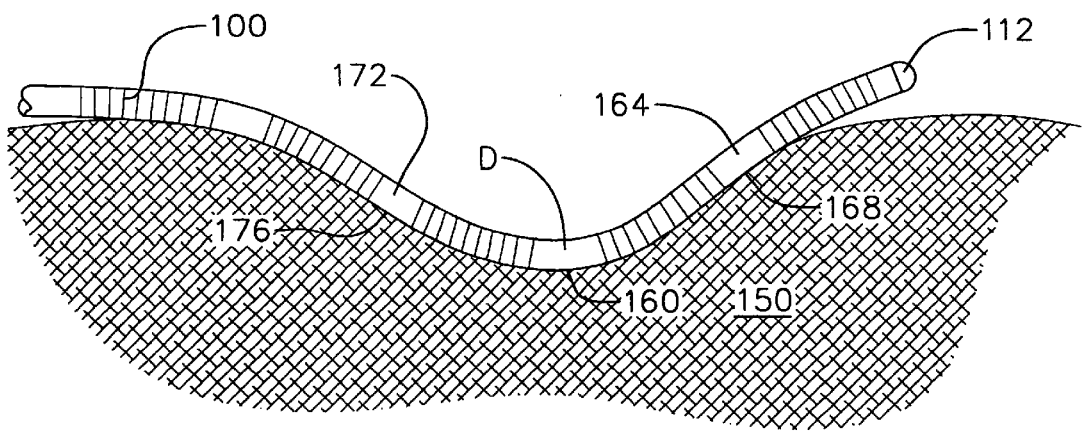

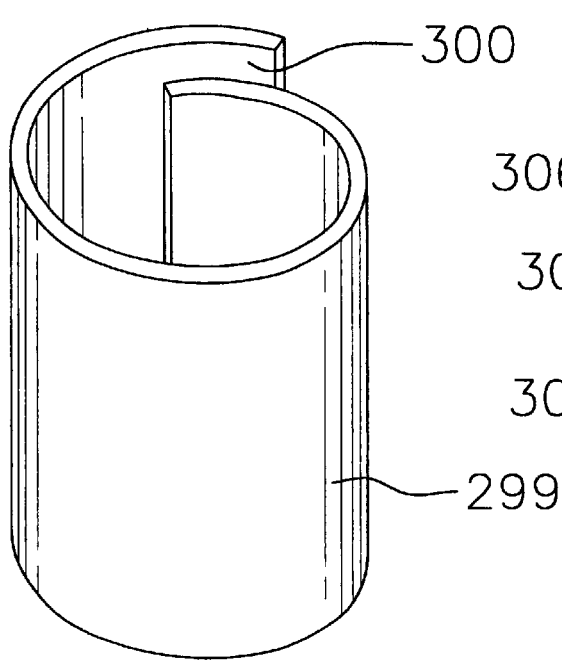
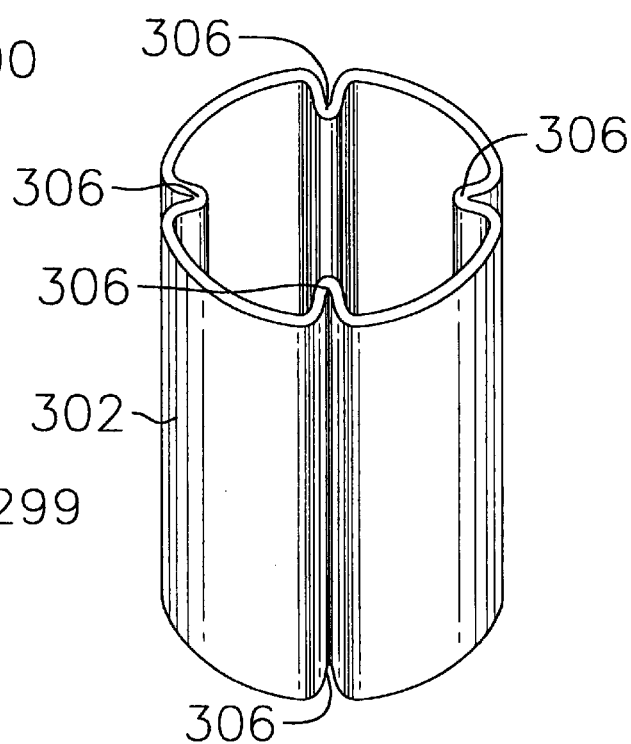
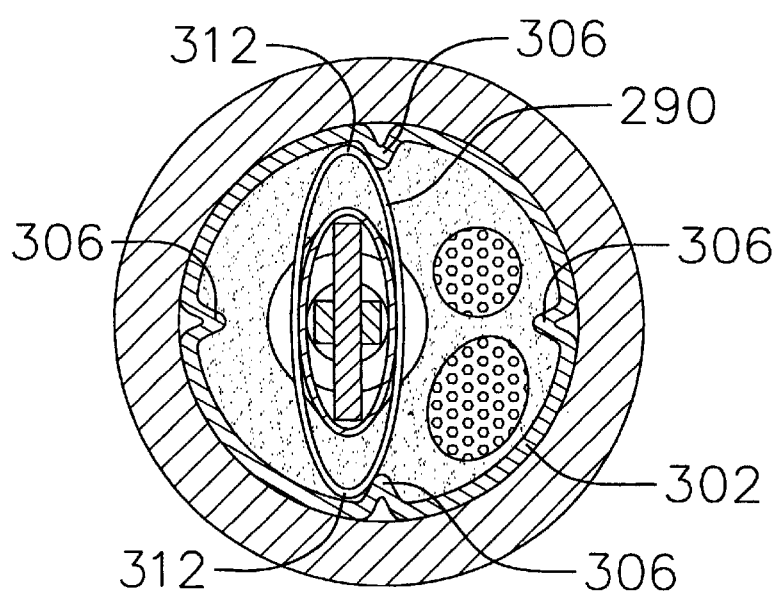

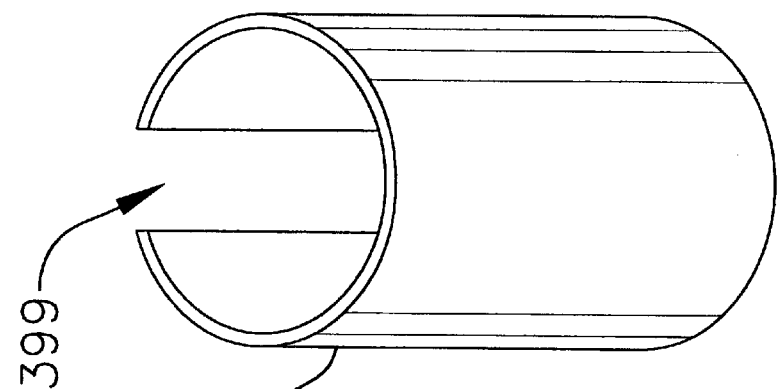
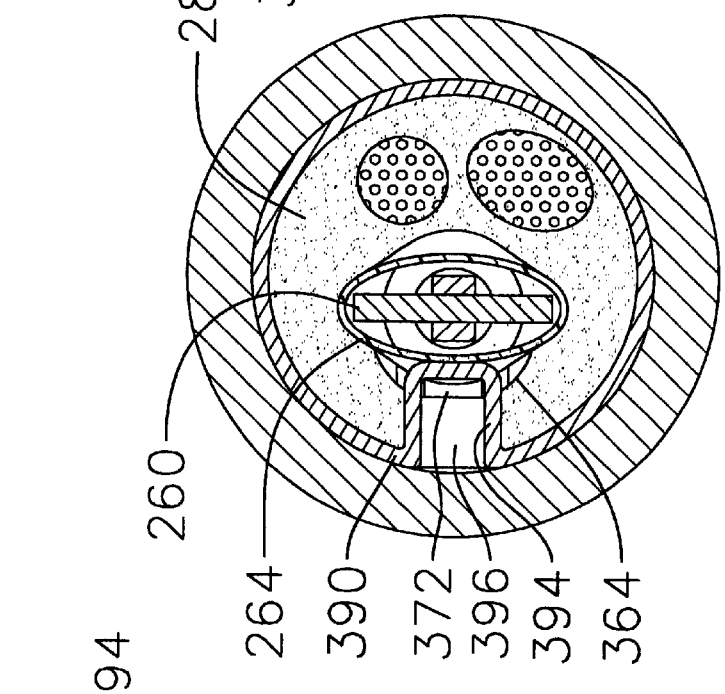
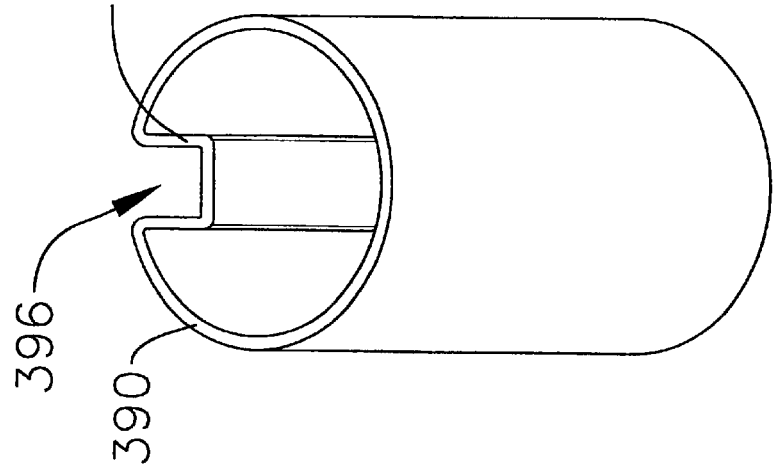

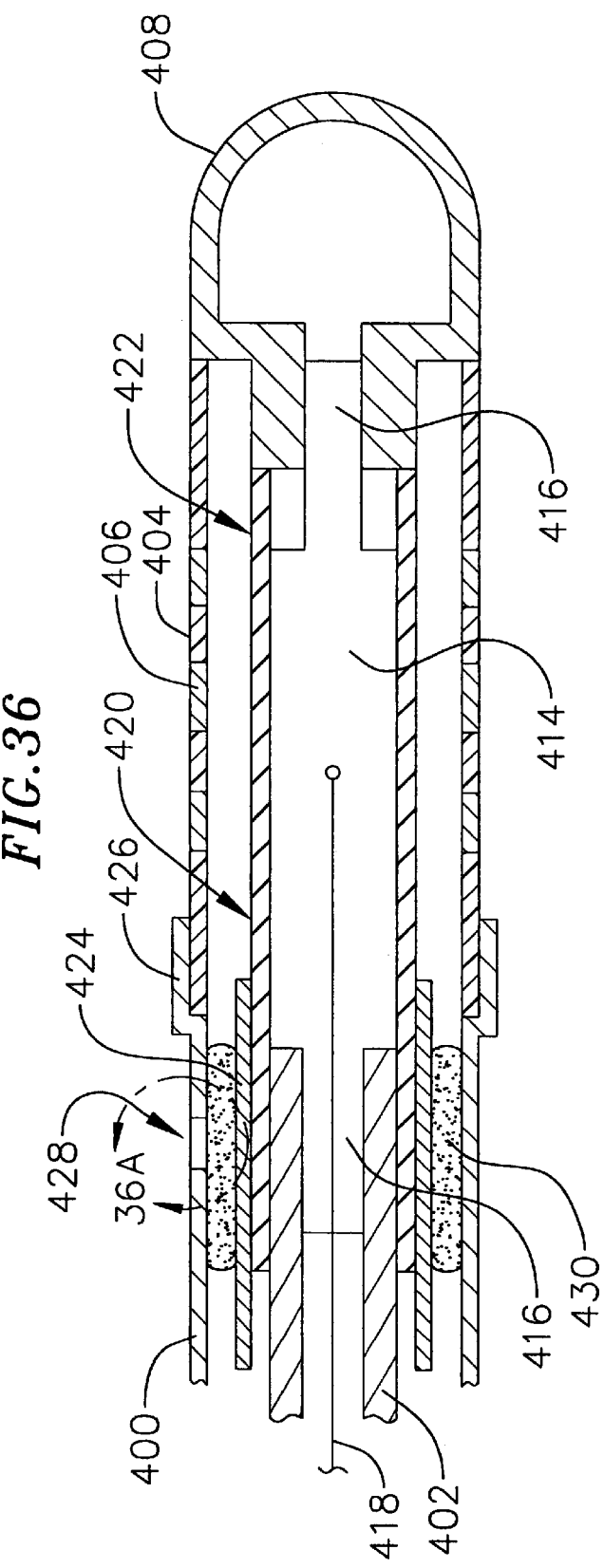

CATHETER HAVING IMPROVED TORQUE TRANSMISSION CAPABILITY AND METHOD OF MAKING THE SAME

CROSS REFERENCE TO RELATED APPLICATIONS

This application is a continuation-in-part of U.S. application Ser. No. 08/902,742, filed Jul. 29, 1997, now abandoned, which is incorporated herein by reference.

BACKGROUND OF THE INVENTIONS

1. Field of the Inventions

The present invention relates generally to catheters.

2. Description of the Related Art

Catheters, which are in widespread medical use today, allow physicians to gain access into interior regions of the body in a minimally invasive manner. Catheters are frequently used to advance electrodes, biopsy devices, and other operative elements through bodily lumens to an intended treatment site. In cardiac treatment, for example, the catheter is steered through a main vein or artery into the region of the heart that is to be treated.

Although precise control of catheter movement is of paramount importance in all catheter-based procedures, the need for careful and precise control over the catheter is especially critical during certain procedures concerning the heart. These procedures, called electrophysiological therapy, are becoming more widespread for treating cardiac rhythm disturbances. Cardiac tissue coagulation (sometimes referred to as "ablation"), where therapeutic lesions are formed in cardiac tissue, is one procedure in which the ability to precisely position the distal end of the catheter is especially important. Incremental distal end movements of 1 mm to precisely position electrode(s) carried on or near the catheter tip are not uncommon and it can take up to an hour to precisely position the tip. In those instances where multiple electrode distal assemblies are employed, it is important that all of the electrodes achieve intimate tissue contact.

Some catheters are steerable in that the distal tip can be manipulated by way of, for example, a distal tip steering mechanism that is operably connected to the catheter handle by a steering control wire. Other catheters are not steerable. Steerable catheters typically include an elongate guide coil that extends from the proximal end of the catheter to a point proximal to the distal end. The steering mechanism consists primarily of a steering center support (also referred to as a "steering spring") that extends from the distal end of the guide coil to the distal tip of the catheter. The inventors herein have determined that the configuration of the steering mechanism in conventional steerable catheters, including the location at which the steering wires are attached to the center support, makes it difficult for conventional catheters to obtain intimate tissue contact.

Whether steerable or not, there are often instances where the physician will attempt to control the position of the distal end of the catheter by rotating the handle at the proximal end. The ability of the physician to precisely control the location of the distal end is directly related to the fidelity of the catheter's transmission of torsional forces exerted on the proximal end to the distal end. The greater the fidelity, the greater the likelihood that the physician will be able to accurately place the electrodes or other operative elements within the patient.

Torque transmission is primarily a function of catheter configuration. Many outer catheter bodies are formed from two tubular parts, or members. The proximal member is relatively long and is attached to a handle, while the distal member, which is relatively short, carries the electrodes or other operative elements. In addition, the proximal member is typically formed from material, such as braided Pebax®, which has better torque transmission properties than the distal member, which is typically formed from a softer, more flexible material such as Pebax®, that is better for steering. The proximal and distal members are adhesive bonded together end to end over a sleeve in what is referred to as a "butt bond" arrangement, which provides some torque transfer between the proximal and distal ends of the catheter. There is also an adhesive bond between the proximal member and steering center support, which is enclosed in a sleeve. This bond forms the primary vehicle for torque transmission from the proximal member to the tip.

The inventors herein have determined that there are a number of shortcomings associated with the conventional arrangement. One shortcoming has to do with the fact that an adhesive bond is formed between a round component, the butt bond sleeve, and the outer surface of the steering sleeve. If the bond is incomplete or if the torque is too strong, the adhesive may break or the steering sleeve may tear, thereby freeing the steering spring to rotate. Also the steering spring may at times freely rotate within the steering sleeve. As a result, there is often adequate torque transmission from the handle to the distal end of the proximal member, but inadequate torque transmission along the distal member, thereby preventing precise tip placement within the patient.

The inventors herein have also determined that the conventional assembly techniques are time consuming and labor intensive, which makes them expensive, and also result in products that may not be as reliable as desired.

SUMMARY OF THE INVENTIONS

Accordingly, the general object of the present inventions is to provide a catheter that avoids, for practical purposes, the aforementioned problems. In particular, one object of the present inventions is to provide a catheter with high fidelity steering. Another object of the present inventions is to provide a catheter having high fidelity torque transmission from the proximal end to the distal tip. Still another object of the present inventions is to provide a catheter that can be manufactured in an economical manner.

In order to accomplish some of these and other objectives, a catheter in accordance with one embodiment of a present invention includes a torque transfer mechanism in the area of the adhesive between the catheter body and an internal component such as, for example, a steering center support (or "steering spring"). The torque transfer mechanism provides enhanced mechanical interference within the adhesive, thereby improving the fidelity of the torque transmission from the proximal member to the catheter tip, as compared to conventional catheters. One example of such a torque transfer mechanism is a crimp sleeve. Another example is a stiffener member including an arm portion that projects into the adhesive. Still another example is a sleeve having radially inwardly projecting ribs. Yet another example is a steering center support having laterally extending portions.

In those implementations employing a butt bond, the torque transfer mechanism may be located within the butt bond sleeve. Alternatively, where an overlapping bond in accordance with another of the inventions herein is employed, the torque transfer mechanism may be located adjacent to the overlapping portions of the proximal and distal catheter body members.

In order to accomplish some of these and other objectives, a catheter in accordance with one embodiment of a present invention is configured such that the steering wires are attached to the center support a suitable distance proximal to the distal end of the center support. In a preferred embodiment, the attachment point is approximately one inch proximal to the distal tip. Such an arrangement provides improved steering and control, as compared to conventional catheters. For example, the distal end of the catheter can be steered into intimate contact with bodily tissue disposed within a tissue crevasse. The catheter can also be steered into a curved shape wherein the distal end portion is relatively straight.

In order to accomplish some of these and other objectives, a catheter in accordance with one embodiment of the present invention includes a hollow catheter body having a side wall and an aperture extending through the side wall, an internal component located within the catheter body, and adhesive material located within the catheter body securing the catheter body to the internal component. There are a number of advantages associated with this embodiment of the present invention. For example, the side wall aperture can be located near the internal component, thereby allowing the adhesive material to be easily injected into the catheter at the desired location. Thus, the present invention may be assembled in a manner that is less labor intensive than conventional methods.

In order to accomplish some of these and other objectives, a catheter in accordance with another embodiment of the present invention includes a hollow catheter body proximal member and distal member respectively located such that a portion of one overlaps a portion of the other, thereby creating an overlapping region, and a bond at the overlapping region securing the proximal member to the distal member. There are a number of advantages associated with this embodiment of the present invention. For example, the surface area of this bond is greater than that of a conventional butt bond, thereby increasing the strength of the bond. Moreover, in those instances where the present bond is a thermal bond, the strength of the bond is additionally increased, as compared to the conventional adhesive bond, because a molecular bond is formed between the catheter body proximal and distal components.

The above described and many other features and attendant advantages of the resent invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 8 is a side elevation view of the distal end steering assembly illustrated in FIG. 6 in a curved configuration disposed within a section of bodily tissue.

FIG. 9 is a side elevation view of the distal end steering assembly illustrated in FIG. 6 being reverse steered into contact with a section of bodily tissue.

FIG. 10 is a side elevation view of the distal end steering assembly illustrated in FIG. 6 in contact with bodily tissue having a crevasse.

FIG. 17A is a perspective view of another crimp sleeve in accordance with a preferred embodiment of a present invention.

FIG. 19 is a perspective view of a ribbed sleeve in accordance with a preferred embodiment of a present invention.

FIG. 20 is a section view of a catheter utilizing the ribbed sleeve illustrated in FIG. 19.

FIG. 32 is a perspective view of a sleeve in accordance with another preferred embodiment of a present invention.

FIG. 33 is a section view of a catheter including the sleeve illustrated in FIG. 32 and the stiffener member illustrated in FIG. 25.

FIG. 34 is a perspective view of a gapped sleeve in accordance with another preferred embodiment of a present invention.

FIG. 36 is a section view of the preferred embodiment illustrated in FIG. 35.

FIG. 36A is an enlarged view of a portion of FIG. 36.

DETAILED DESCRIPTION OF THE PREFERRED EMBODIMENTS

The following is a detailed description of the best presently known mode of carrying out the inventions. This description is not to be taken in a limiting sense, but is made merely for the purpose of illustrating the general principles of the inventions.

The detailed description of the preferred embodiments is organized as follows:

I. Introduction
II. Steering
Ill. Torque Transmission
IV. Alternative Bond Configurations The section titles and overall organization of the present detailed description are for the purpose of convenience only and are not intended to limit the present inventions.

I. Introduction

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of arrhythmia conditions within the heart. Other applications include the diagnosis or treatment of intravascular ailments in association with, for example, angioplasty or atherectomy techniques. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. A physician is able to position the distal section, which may include diagnostic and/or soft tissue coagulation electrodes in the form of rings or coils (also referred to as "ablation electrodes"), into contact with tissue and use a reverse steering technique to improve tissue contact. For example, the distal section of a catheter in accordance with a present invention will conform to non-uniform anatomic regions such as the Eustachian ridge between the inferior vena cava and the tricuspid annulus.

Figure 1:
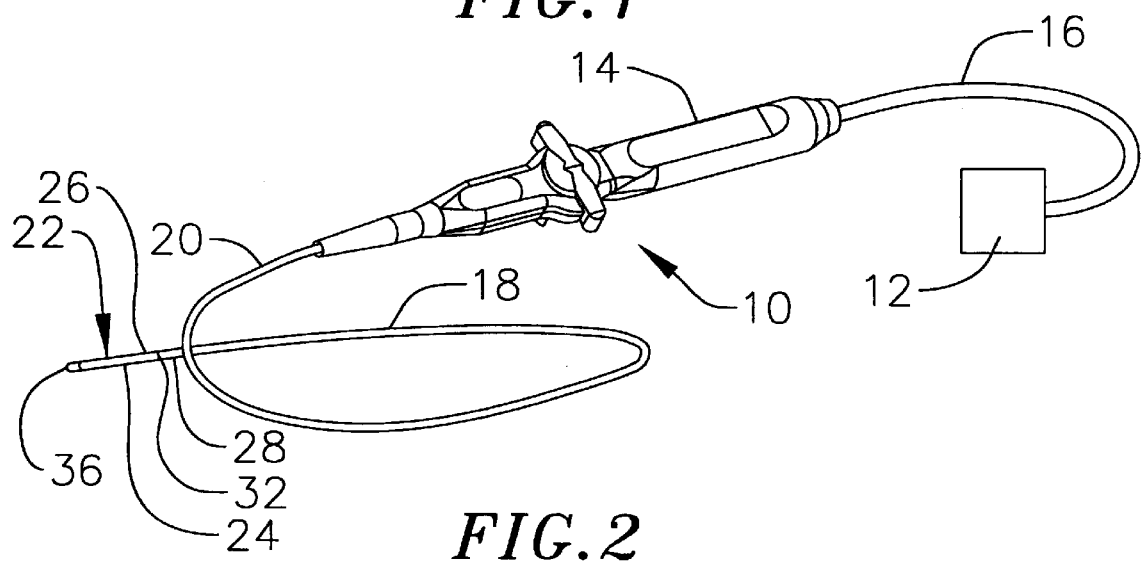
FIG. 1 is a perspective view of a catheter in accordance with a preferred embodiment of a present invention.

A catheter system 10 in accordance with a preferred embodiment of the present invention is illustrated in FIG. 1. The illustrated embodiment includes a handle 14, a system controller 12 that is connected by an electrical cable 16 to the handle 14, a main body tube (or "proximal member") 18, and a distal end assembly 22 including a section of distal end tube (or "distal member") 24. The main body tube 18 is engaged at its proximal end 20 to the handle 14, and at its distal end 28 to the proximal end 26 of the distal end tube 24 by a bond 32. The exemplary catheter system also includes a tip member 36. Alternately, a tip electrode may be employed. A steering mechanism is disposed within the distal end assembly 22 and is connected to the handle 14 through steering wires that pass through the main body tube 18.

The system controller is preferably one which will simultaneously supply power to a plurality of electrodes with temperature feedback and control. The electrodes are preferably shorter than those used in conventional catheters and are spaced close together. These features facilitate the production a variety of lesions, including large surface area, deep lesions and continuous long thin lesions. As such, the catheter is especially useful in treating atrial flutter, atrial fibrillation, other supraventricular tachycardias, and ventricular tachycardia substrates. The preferred electrode configuration also provides more detailed mapping capabilities.

II. Steering
A. Conventional Devices

Figure 2:
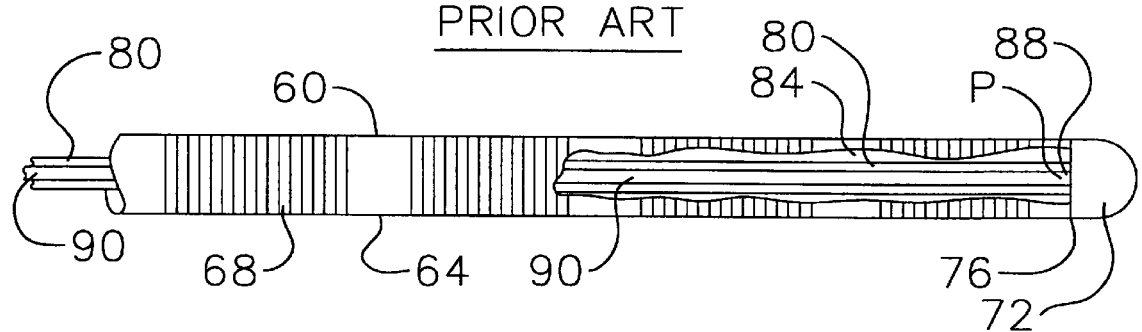
FIG. 2 is a side elevation view, with cut away portions, of a prior art distal end assembly.

To provide an understanding of the technology relevant to this disclosure, a prior art catheter distal end assembly 60 is illustrated in FIG. 2. The distal end assembly 60 includes a hollow tubular body portion 64 having a plurality of ablation electrodes 68 disposed along its length. A tip member 72 is located at the distal end 76 of the tubular member 64. A thin flat steering center support 80 is disposed within the central lumen 84 of the tubular member 64. The tip member 72 is fixedly engaged to the distal end 88 of the center support 80. Two steering wires 90 and 92 are bonded to opposite sides of the center support 80 at a location P at the distal end 88 of the center support 80, immediately behind the tip member 72 (only wire 90 is shown in this view).

Figure 3:
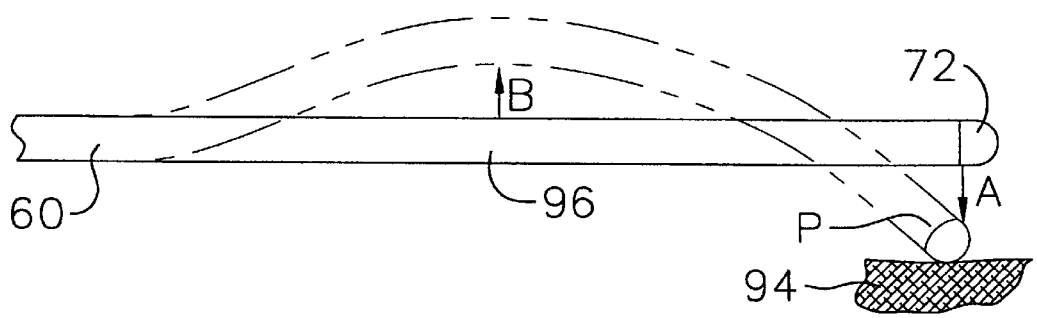
FIG. 3 is a side elevation view of the steering distortion characteristics of the prior art distal end assembly.

The inventors herein have determined that various positioning control and performance difficulties may be experienced with the prior art device 60. As illustrated in FIG. 3, certain steering maneuvers, particularly reverse steering (where the tip 72 is deflected a distance A in one direction to make contact with tissue 94), can cause proximal portion 96 extend a distance B in the direction opposite to the movement direction of the tip 72, thus causing a snake-like effect. This effect is undesirable for catheters carrying multiple ablation electrodes because it causes electrodes in the region 96 to extend away from tissue that is to be treated. This undesirable effect is due to the flexibility of the distal end 60 and apparently results because the point of maximal steering force is proximal to the steering wire attachment point P.

Figure 4:
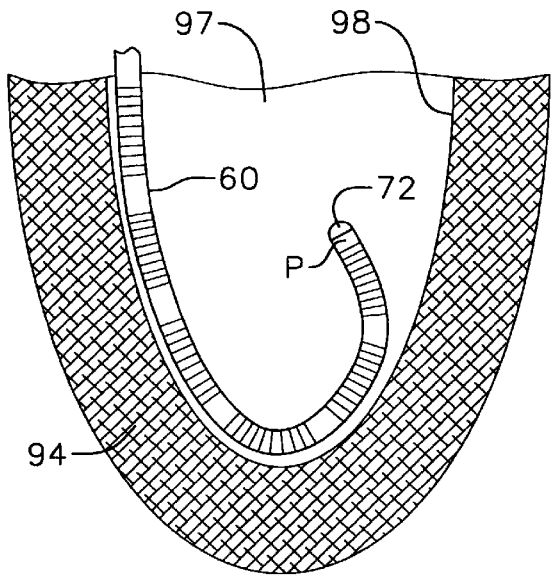
FIG. 4 is a side elevation view of the prior art distal end assembly in a curved configuration disposed within a section of bodily tissue.
Figure 5:
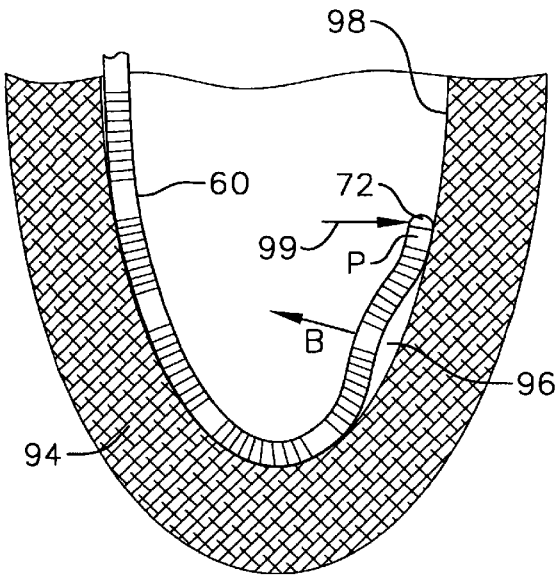
FIG. 5 is a side elevation view of the prior art distal end assembly being reverse steered into a section of bodily tissue.

FIG. 4 depicts the prior art device 60 in a curved configuration disposed within a cavity 97 of bodily tissue 94. Such a cavity is representative of a heart ventricle. Once the device 60 is steered to an appropriate location within the cavity 97, it is steered into a curve or loop that is tighter than the inner wall 98 of the cavity 97. Thereafter, as illustrated in FIG. 5, it is reverse steered (see arrow 99) to open the loop in order to press the sides of the device 60 against the surface 98. As is illustrated in FIG. 5, when the device 60 is reverse steered, such that the tip 72 makes contact with the surface 98 of the tissue 94, an undesirable gap B in region 96 may be created. This results in less than satisfactory contact between the device 60 and the tissue surface 98.

B. Exemplary Embodiments of a Present Invention

Figure 6:
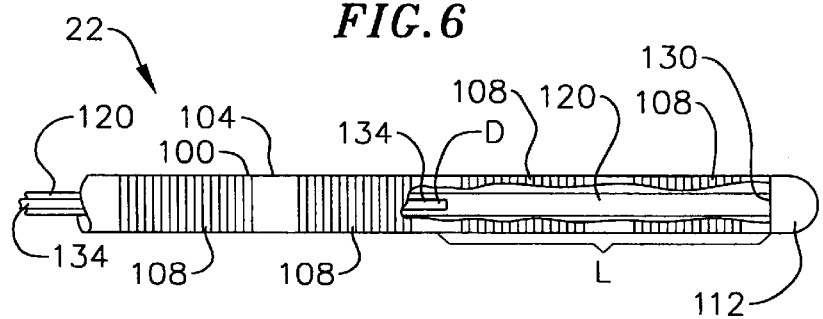
FIG. 6 is a side elevation view, having cut away portions, of a distal end steering assembly in accordance with a preferred embodiment of a present invention.

As shown by way of example in FIG. 6, one embodiment of a present invention solves this problem in the art by relocating the steering wire attachment point away from the distal end of the steering center support. The exemplary catheter distal end assembly 100 illustrated in FIG. 6 includes a tubular body portion 104 having a plurality of ablation (or "soft tissue coagulation") electrodes 108 disposed throughout its length. A flat steering center support 120 is centrally disposed within the tubular member 104 and a tip member 112 is engaged to the distal end 130 of the center support. Two steering wires 134 and 138 are disposed on opposite sides of the center support 120 (wire 138 is not shown in this view). The steering wires 134 and 138 are affixed (such as by soldering, welding or bonding) to opposite sides of the center support 120 at a point D which is located a distance L proximal to the distal end 130 of the center support. In the preferred embodiment illustrated in FIG. 6, the distance L is approximately one inch so that the electrodes 108 are located distally of the steering wire attachment point D.

Other steering wire positioning concepts are described in U.S. Pat. No. 5,273,535, entitled "Catheter with Electrode Tip Having Asymmetric Left and Right Curve Configurations," which is incorporated herein by reference.

Figure 7:
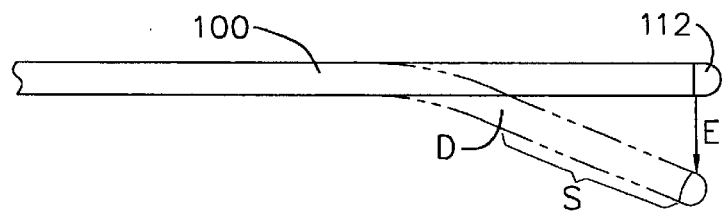
FIG. 7 is a side elevation view of the distal end steering assembly illustrated in FIG. 6 showing the steering distortion characteristics thereof.

The deflection profile of the exemplary catheter distal end assembly 100 is illustrated in FIG. 7, where actuation of the steering wires 134 and 138 has caused the tip 112 to deflect a distance E. The location of the steering wire attachment point D produces an advantageous steering profile which increases the force exerted against tissue with the ablation electrodes located proximal to the attachment point D. In addition, locating the attachment point D proximal to the distal tip produces a relatively straight region distal to the attachment point when steering is actuated. For certain applications, the portion of the catheter distal end assembly 100 that is located distally of the steering wire attachment point D can be made more or less flexible than other portions of the end assembly 100. The degree of flexibility or stiffness of this distally located portion is a matter of design choice, depending upon the specific application in which the particular catheter end assembly is to be utilized.

FIG. 8 depicts the catheter distal end assembly 100 disposed within a cavity 97 of a body tissue member 94, such as a heart ventricle, while FIG. 9 depicts the assembly being reverse steered (arrow 99) within the cavity. A comparison of the movement of the exemplary catheter end assembly 100 (FIGS. 8 and 9) to the movement of the prior art device 60 (FIGS. 4 and 5) shows that when the present distal end assembly 100 is reverse steered to achieve intimate tissue contact with the surface 98, uniformly intimate tissue contact is created at point D by the present assembly. This results in improved diagnostic and therapeutic performance as compared to the prior art device 60. The present catheter does not lift off the tissue proximal to point D because of the spring force of the catheter when it is in its prolapsed position illustrated in FIG. 9.

The improved steering and performance characteristics of the present catheter distal end assembly 100 are particularly evident when the device is utilized to map or ablate tissue regions having nonuniform anatomical features, including crevasses such as in the Eustachian ridge region of the heart. In addition, this system enables the controllable creation of long, deep lesions which may be located between infarct zones or from an infarct zone to an anatomic barrier, as illustrated in FIG. 10. Here, a cross-section of tissue 150 is illustrated having a crevasse 160 which represents the Eustachian ridge region. The distal end assembly 100 is placed across the crevasse 160, such that the steering wire attachment point D is located approximately in the center of the crevasse. When the steering wires are actuated to draw the distal end assembly 100 down into the crevasse 160, the portion 164 of the assembly that is located distal to the attachment point D is forced upwards against one side 168 of the crevasse, whereas the portion 172 of the assembly located proximal to the attachment point D is pressed against the other side 176. As such, the distal end assembly 100 advantageously fills and makes intimate contact with tissue on both sides of the crevasse 160.

Figure 11:
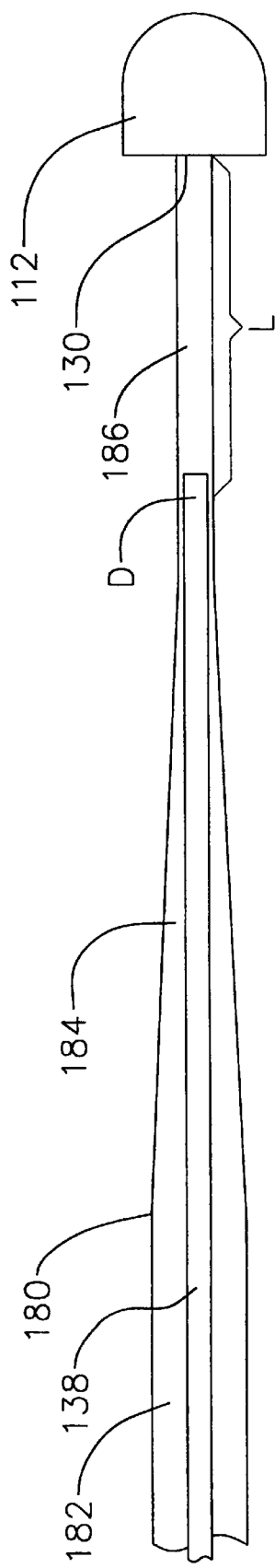
FIG. 11 is a side elevation view of a tapered center support in accordance with a preferred embodiment of a present invention.

To better enable the distal end assembly 100 to fill a crevasse, portions of the assembly 100 proximate the attachment point D may be constructed such that they are particularly flexible. One example of a relatively flexible tapered steering center support 180 is shown in FIG. 11. As illustrated FIG. 11, the exemplary tapered center support 180 is formed with a relatively wide proximal section 182, a tapered middle section 184 and a relatively narrow distal end portion 186. A tip member 112 is fixedly engaged to the distal end 130 of the center support 180. The steering wire 138 is attached to the center support 180 in the thin distal portion 186 at a distance L from the distal end 130. The attachment point D is therefore located in the most flexible region of the center support 180. The enhanced flexibility of this steering attachment point enables a distal end assembly utilizing center support 180 to conform to tissue having ridges and crevasses, as is illustrated in FIG. 10. Alternatively, the center support may be modified such that it has a more flexible wire between the attachment point D and the distal tip of the catheter.

Figure 12:
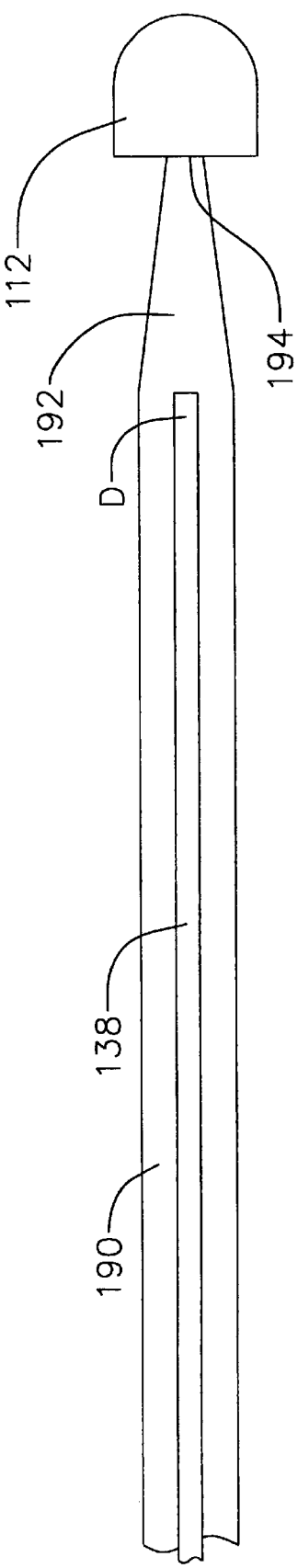
FIG. 12 is a side elevation view of a tapered center support in accordance with another preferred embodiment of a present invention.

As illustrated in FIG. 12, an alternative center support 190 is formed with a constant width through steering wire attachment point D. Thereafter, a tapered section 192 proceeds distally to a distal end 194. It will be appreciated that the center support 190 will possess different stiffness characteristics than the center support 180 and may be used in different applications.

C. Applications

This present catheter may be used to create various lesion types. Long, transmural lesions may be created in the atria to cure atrial fibrillation or atrial flutter. The catheter distal end assembly 100 may be placed in intimate contact with any portion of the atrial endocardium to produce curvilinear lesions capable of curing atrial fibrillation. The steering modifications and distal section designs described herein improve tissue contact when the catheter is prolapsed and reverse steered.

Discrete lesions may be created to treat other supraventricular tachycardias. Such lesions are created when a subset of the electrodes used to map the arrhythmia substrate are used to create the desired lesion thus terminating the arrhythmia substrate. By using the same electrodes(s) to create the lesion(s) as were used to map the substrate, more accurate lesion placement is assured and catheter repositioning required to map and ablate the substrate is reduced.

Large surface area, shallow lesions or large surface area, deep lesions may be created to ablate ventricular tachycardia substrates, especially those associated with monomorphic ventricular tachycardia. Energy delivery time and tissue temperature may be adjusted to create the desired lesion geometry.

Long, transmural lesions may also be created in the atria from an incision previously created during a surgical procedure to an anatomic barrier. Anatomic barriers are structures such as the tricuspid valve annulus, mitral valve annulus, and vein orifices through which depolarization waveforms do not propagate. Depolarization waveforms may propagate around incisions and anatomic barriers producing reentrant tachyarrhythmias, but lesions connecting such structures reduce the potential for reentrant propagation patterns. Related devices are taught in co-pending U.S. patent application Ser. No. 08/788,782, entitled "Systems and Methods for Controlling Tissue Ablation using Multiple Temperature Sensing Elements," and Ser. No. 08/769,856, entitled "Loop Structures for Supporting Multiple Electrode Elements," which are incorporated herein by reference.

Long, deep lesions created in the ventricles with the catheter distal end assembly 100 may be used to create lesions between infarcted regions (determined by reviewing intracardiac electrograms, impedance mapping, ultrasound, or other technique) or from an infarcted region to an anatomic structure to treat ventricular tachycardias. This may be especially useful for polymorphic ventricular tachycardia substrates. Related devices are taught in co-pending U.S. patent application Ser. No. 08/738,822, entitled "Systems and Methods for Visualizing Interior Regions of the Body," which is incorporated herein by reference.

A catheter including the exemplary distal end assembly 100 has been demonstrated to facilitate the creation of an atrial flutter curing lesion in vivo. In particular, electrodes on the assembly were readily placed at the junction between the inferior vena cava and the tricuspid annulus. The steering created intimate contact with electrodes contacting the endocardial surface and caused electrodes to fill the Eustachian ridge. When radiofrequency energy was transmitted to all desired electrodes simultaneously, a contiguous lesion was created which was continuous in the subepicardial space.

The catheter was also utilized to create ventricular lesions. In particular, lesions were created that measured 3 cm in length and more than 7 mm in depth. These lesion dimensions actually underestimate the actual lesion dimensions because the heart was dissected soon after lesion creation and the heart was grossly viewed for color changes without pathological staining. As a result, the actual lesion depths were greater than 1 cm. The exemplary catheter distal end assembly 100 was easily placed on the endocardial surface and reverse steered to obtain intimate tissue contact of the ablation electrodes and used to create long, deep lesions capable of curing ventricular tachycardia. In fact, the present catheter has enabled users to terminate ventricular tachycardia in three of three animal experiments having an infarct model of ventricular tachycardia.

Ill. Torque Transfer

In accordance with another invention herein, mechanisms for improving the transfer of torque from the main body tube (or "proximal member") 18 to the distal assembly 22 are provided. In one implementation of the invention, the focus is on torque transfer at the butt bond joint 32 between the main body tube 18 and the distal end assembly 22. However, the invention is also applicable to other types of joints and bonding arrangements that may be used to secure the main body tube 18 to the distal end assembly 22, such as the novel arrangements described in Section IV below.

A. Conventional Devices

Figures 13, 14:
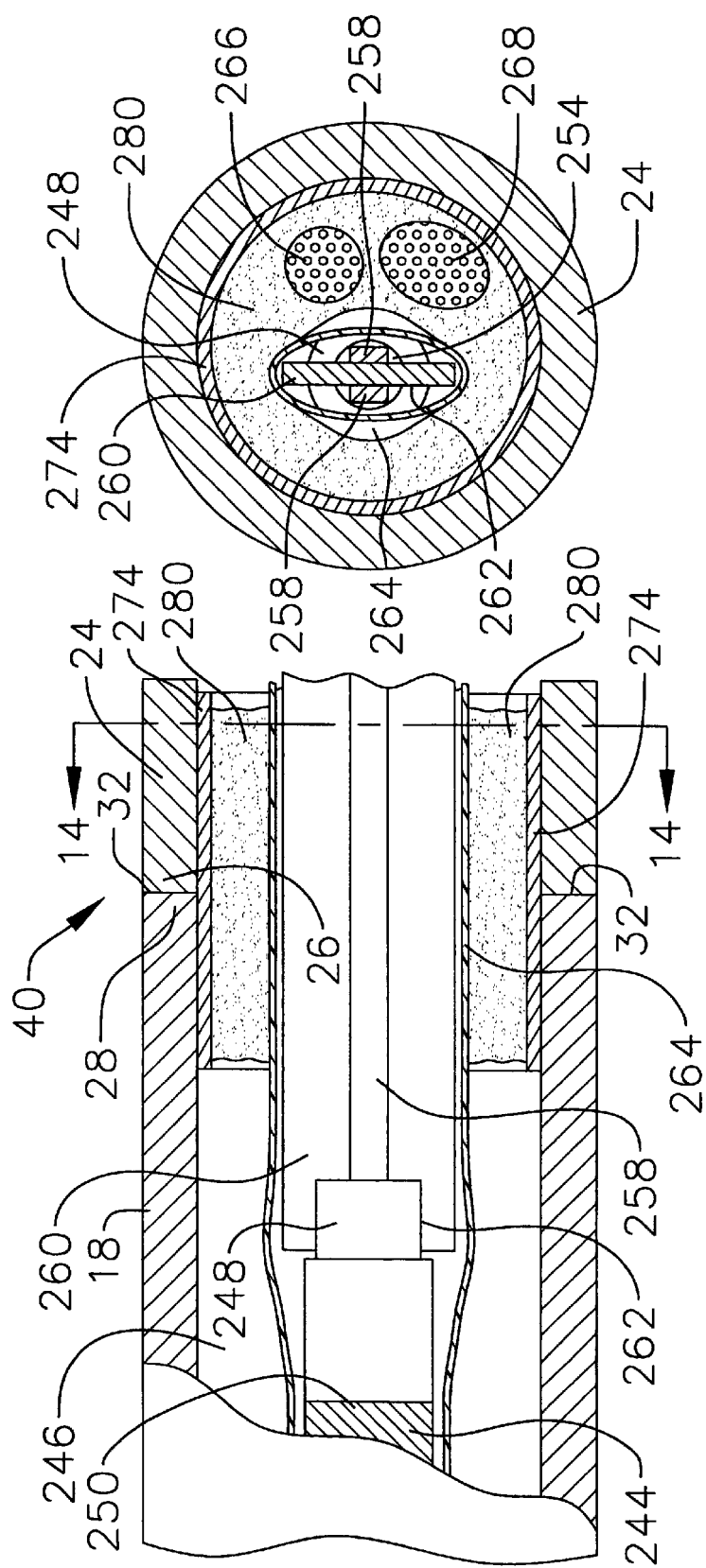
FIG. 13 is a side elevation view, having cut away sections, of a prior art distal end butt bond assembly.
FIG. 14 is a section view taken along lines 14—14 in FIG. 13.

Referring first to FIGS. 13 and 14, which show a prior art butt bond joint assembly 240, the main body tube 18 is generally formed of a braided material for strength, push-ability and efficient torque transfer throughout its length. A tubular steering mechanism guide coil 244 is disposed within the central lumen 246 of the main body tube 18 and a steering ferrule 248 is engaged to the distal end 250 of the guide coil. The steering ferrule 248 is formed with a steering wire bore 254 therethrough so that steering wires 258 disposed within the guide coil 244 project through the bore towards the distal end of the assembly 22. A flat steering center support 260 is disposed within a slot 262 that is formed through the distal portion of the ferrule 248. An insulating shrink tube 264 is formed around the steering mechanism which includes the distal portion of the guide coil 244, the ferrule 248, steering center support 260 and steering wires 258. Other components, such as bundled electrode wires 266 and temperature sensor wires 268, may also be disposed within the lumen 246. The proximal end 26 of the distal end tube 24 is adhesively butt bonded (note reference numeral 32) to the distal end 28 of the main body tube 18. To provide strength to the butt bond 32, a tubular butt bond sleeve 274 is disposed within the butt bond joint assembly 240, and both the distal end 28 of the main body tube 18 and the proximal end 26 of the distal end tube 24 are adhesively bonded to the butt bond sleeve 274 in addition to being butt bonded to one another. A quantity of adhesive material 280 is also inserted into the butt bond sleeve 274 to bond the steering mechanism sleeve 264 within the butt bond sleeve 274.

When the main body tube 18 is rotated, it is desirable that the torque be communicated to the distal end assembly 22. To achieve this, the torque at the distal end 28 of the main body tube 18 is transferred to the distal end assembly 22 through the butt bond joint 240, primarily from the butt bonding sleeve 274, to the steering center support 260 through the adhesive material 280 within the butt bond sleeve 274. Torque forces are also transferred from the main body tube 18, through the butt bond 32 to the proximal end 26 of the distal end tube 24.

B. Exemplary Embodiments of a Present Invention

Figure 16:
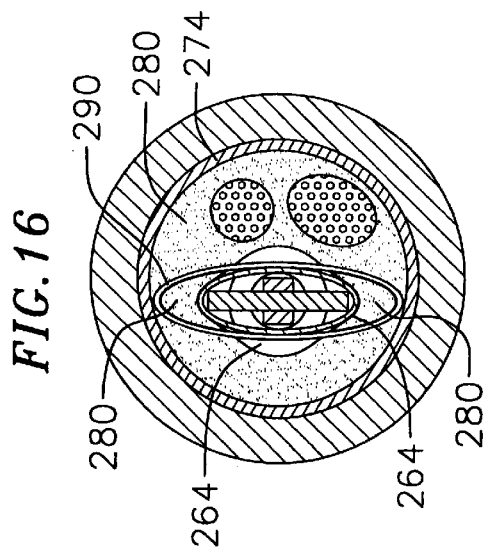
FIG. 16 is a section view taken along line 16—16 in FIG. 15.
Figure 15:
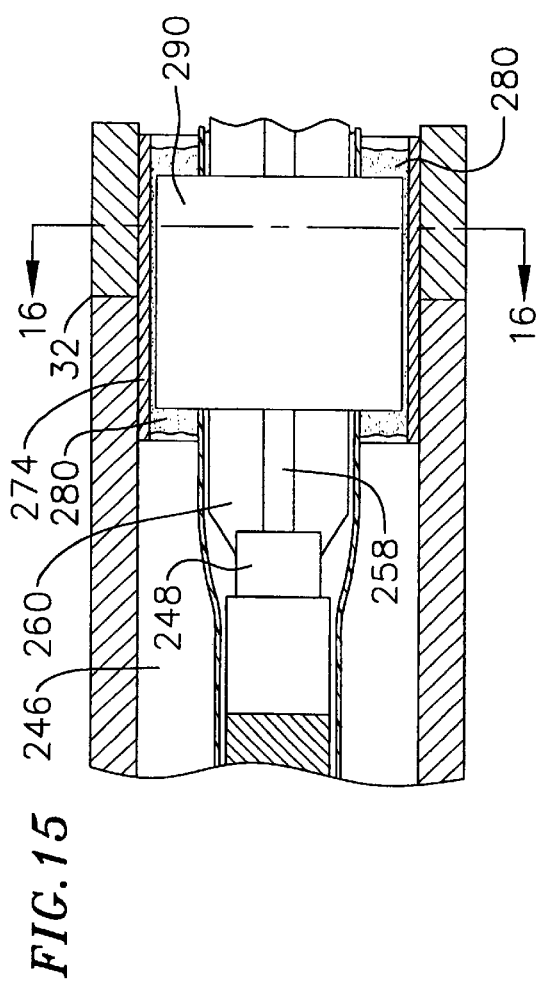
FIG. 15 is a side elevation view, having cut away portions, of a catheter having a torque transfer device in accordance with a preferred embodiment of a present invention.

A first preferred embodiment of a torque transfer device in accordance with a present invention is illustrated in FIGS. 15 and 16. Here, the torque transfer device is in the form of a generally oval crimp sleeve 290 that is disposed around the steering sleeve 264. In the illustrated embodiment, the crimp sleeve 290 is located within the butt bond sleeve 274. A quantity of adhesive material 280, such as cyanoacrylate or an epoxy, is injected into the butt bond sleeve 274 when the device is assembled. The adhesive material 280 serves to bond all of the components together within the butt bond sleeve 274 and within the crimp sleeve 290, thereby providing improved torque transfer as compared to the prior art device illustrated in FIGS. 13 and 14. However, in those implementations where a butt bond is not employed, the adhesive material 280 and crimp sleeve 290 will simply be located in the region where the proximal and distal catheter tubes (or "members") are secured to one another.

In one embodiment, the crimp sleeve 290 is a cut length of metal hypodermic tubing or the like. In assembling the catheter 10, the guide coil 244, ferrule 248, center support 260 and steering wires 258 are first assembled. The polyester shrink tube steering sleeve 264 is then placed over the assembly. The round crimp sleeve 290 is then placed over the steering sleeve 264 in the location of the butt bond 32 (or other bond when a butt bond is not employed) and crimped into an oval of appropriate size to fit over the steering assembly. The steering sleeve 264 is crimped to make a close fit with the steering assembly, but not pinch the steering wires 258, which would impede the steering capability of the device. The steering assembly with its guide coil 244 is then inserted into the main body tube 18, such that the crimp sleeve 290 of the steering assembly is located at the butt bond 32 location. The butt bond sleeve 274 is placed in position surrounding the crimp sleeve 290 while adhesive material 280 is applied to the butt bond area. The adhesive material 280 is injected between the butt bond sleeve 274 and the crimp sleeve 290, as well as within the crimp sleeve 290 exterior to the steering sleeve 264. The proximal end 26 of the distal tube 24 is then adhered to the butt bond sleeve 274 and to the distal end 28 of the main body tube 18 to complete the assembly. Upon the hardening or curing of the adhesive material, the improved torque transfer device is completed.

The improved torque transfer capabilities associated with the present invention are the result of the increased mechanical interference between the center support 260 of the steering assembly within the crimp sleeve 290, together with the improved, metal to metal bond, and improved mechanical keying of the crimp sleeve 290 within the butt bond sleeve 274. As a result of the utilization of the crimp sleeve 290, torque from the main body tube 18 is efficiently transferred through the butt bond sleeve 274 to the crimp sleeve 290 and ultimately to the center support 260 of the steering assembly. Of course, in implementations where a butt bond is not employed, the torque will be transferred directly from the main body tube 18 to the crimp sleeve 290.

In the preferred catheter distal end assembly, the catheter tip 36 is fixedly engaged to the distal end of the center support 260 by, for example, soldering, welding or adhesive bonding. The torque is therefore efficiently transmitted to the tip 36, such that torque is applied to the distal tubing 24 at both its proximal end 26 by the butt bond 32 (or other type of bond) and the distal end by the catheter tip 36. This provides improved delivery of torque to various components, such as electrodes, that may be disposed along the length of the distal tube 24.

Figure 18:
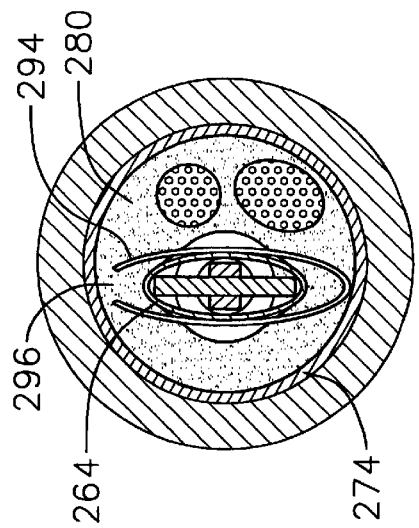
FIG. 18 is a section view of a catheter utilizing the crimp sleeve illustrated in FIG. 17.
Figure 17:
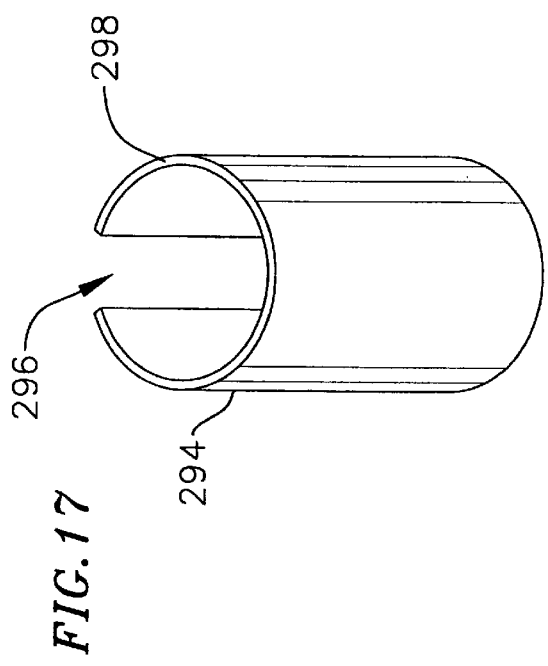
FIG. 17 is a perspective view of a crimp sleeve in accordance with a preferred embodiment of a present invention.

In accordance with another preferred embodiment, a "C" shaped crimp sleeve 294 having a gap 296 in its sidewall 298 can be utilized in place of the tubular crimp sleeve 290 illustrated in FIGS. 15 and 16. As shown by way of example in FIGS. 17 and 18, the "C" shaped crimp sleeve 294 can be placed around the steering sleeve 264 at the location of the butt bond 32 (or other bond) and crimped in place. Such a "C" shaped crimp sleeve 294 is somewhat easier to put in place than the tubular crimp sleeve 290 because it may be inserted laterally onto the steering sleeve 264, utilizing the sidewall gap 296 rather than being installed axially down the steering sleeve 264, as is tubular crimp sleeve 290. A "U" shaped crimp sleeve may also be used.

A "G" shaped crimp sleeve 299 is illustrated in FIG. 17A. The crimp sleeve 299 is formed with a generally spiral shaped gap 300 which becomes closed when the sleeve 299 is crimped around the steering assembly. The crimp sleeve 299 can therefore be thought of as a hybrid combination of the tubular crimp sleeve 290 and the "C" shaped crimp sleeve 294.

In accordance with another invention herein, and as illustrated in FIGS. 19 and 20, a sleeve 302 is formed with a plurality of radially inwardly projecting ribs 306 that are parallel to the longitudinal axis of the generally cylindrical sleeve. The sleeve can be used as a butt bond sleeve in an implementation employing a butt bond or to simply improve torque transfer in implementations that do not employ a butt bond. Referring specifically to FIG. 20, the ribs 306 provide additional torque transfer capability by providing a mechanical interaction with the outer portions 312 of the crimp sleeve 290. The space between the sleeve 302 and the crimp sleeve 290 is preferably filled with adhesive material 280. Although four ribs 306 are illustrated in FIGS. 19 and 20, the invention is not so limited and fewer or more ribs may be employed.

Figure 21:
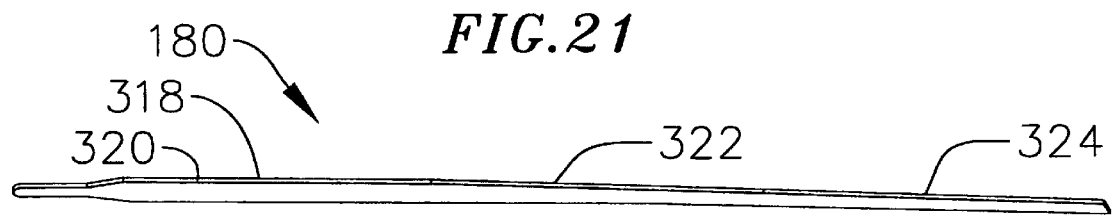
FIG. 21 is a perspective view of a steering center support in accordance with a preferred embodiment of a present invention.

To further aid in the transfer of torque to the center support 260, the width of the center support 260 may be increased within the butt bond (or other bond) area. As illustrated for example in FIG. 21, a center support 318, which is substantially identical to center support 180 illustrated in FIG. 11, is formed with a relatively wide proximal end 320 for the efficient transfer of torque to the center support. Center support 318 also includes a tapered central section 322 and a relatively narrow distal end 324. The relatively wide proximal end 320 serves to increase the mechanical keying of the center support 318 within the crimp sleeve 290, while the tapered central section 322 and relatively thin distal section 324 provide a generally increased flexibility towards the distal end of the catheter distal end assembly 24, as compared to its proximal end. As discussed in Section II above, such varying flexibility throughout the length of the catheter distal end assembly 24 has been shown to provide improved catheter distal end steering and control properties. Therefore, a preferred embodiment of the present invention includes the tapered steering center support 318 disposed within the crimp sleeve 290.

In another alternative design, the crimp sleeve 290 may be captured in a thermally formed bond between the main body tube 18 and the distal tube 24. The crimp sleeve would be embedded in the thermally melted wall formed inside the tube bond transition similar to being captured in the adhesive bond. This would also provide an enhanced mechanical interference fit for improved torque transfer. This design would be identical to those shown in FIGS. 16 or 30 except that the butt bond sleeve would be omitted.

Figure 22:
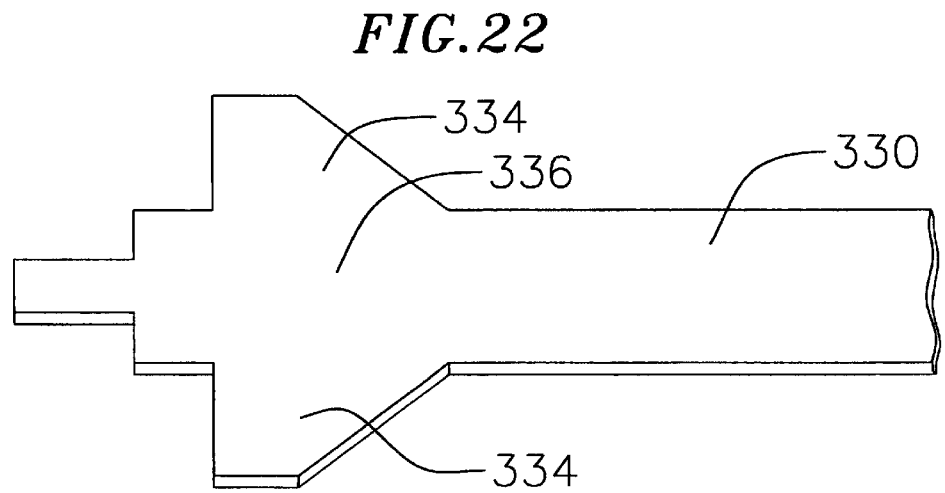
FIG. 22 is a perspective view of another steering center support in accordance with a preferred embodiment of a present invention.
Figure 23:
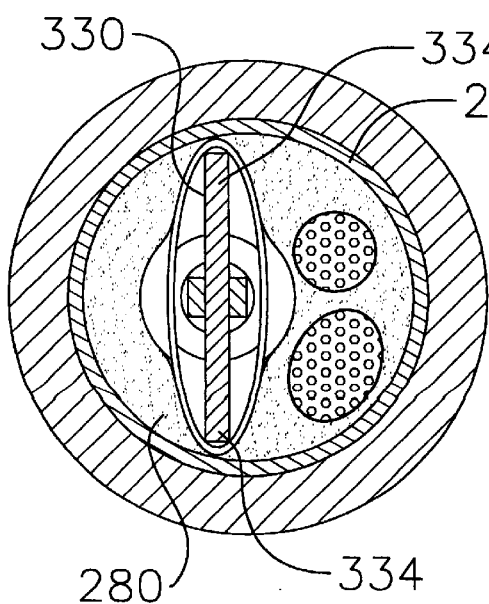
FIG. 23 is a section view of a catheter utilizing the steering center support illustrated in FIG. 22.

Still another alternative steering center support 330 is illustrated in FIG. 22. The center support 330 is formed with lateral extending portions 334 that are located along the proximal portion 336 of the center support 330 that will be disposed within the butt bond sleeve 274 or in the area of other types of bonds that join the catheter body proximal and distal members. The lateral extending portions 334 serve to provide even further mechanical interference and torque transfer when they are disposed within a crimp sleeve 290 than the previously described center supports 318 and 260. The center support 330 also provides improved torque transfer over the prior art illustrated in FIGS. 13 and 14, even where a crimp sleeve 290 is not utilized. Specifically, as illustrated in FIG. 23, the lateral extensions 334, even when just disposed within a steering sleeve 264, provide enhanced mechanical interference with the adhesive material 280.

Figure 24:
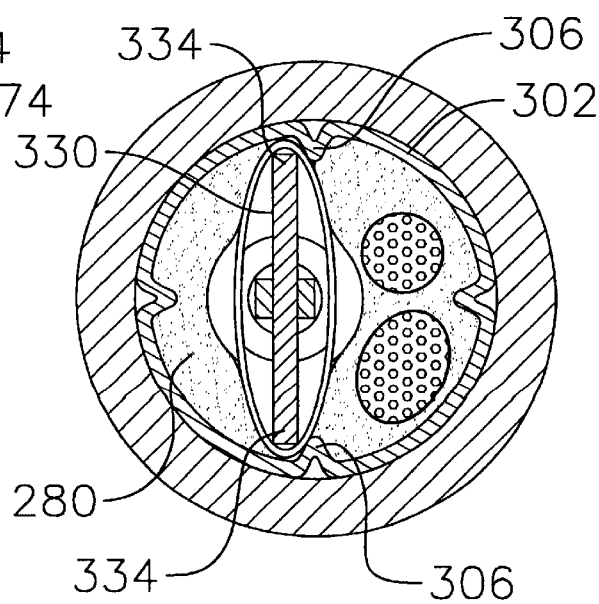
FIG. 24 is an end elevation view of a catheter utilizing the ribbed sleeve illustrated in FIG. 19 and the steering center support in FIG. 22.
Figure 25:
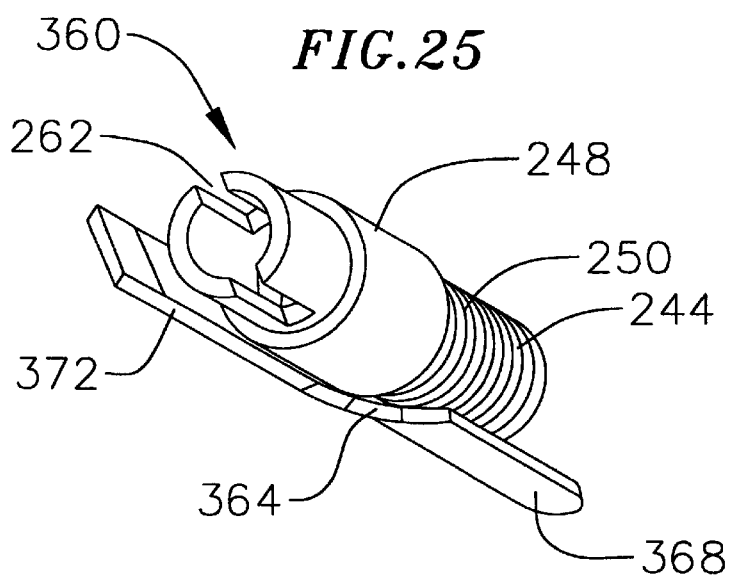
FIG. 25 is a perspective view of a stiffener member in accordance with a preferred embodiment of a present invention.
Figure 26:
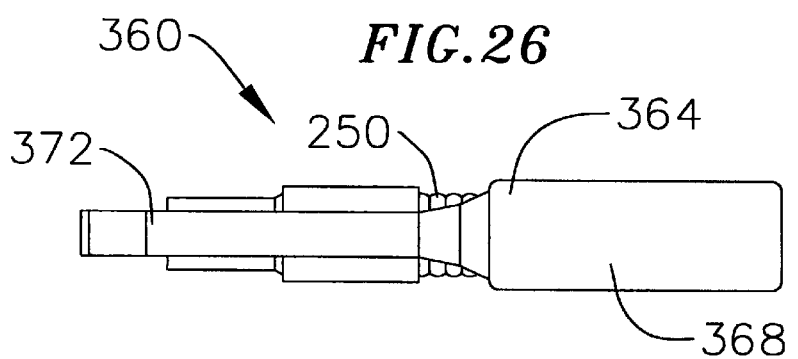
FIG. 26 is a top plan view of the stiffener member illustrated in FIG. 25.
Figures 27, 28:
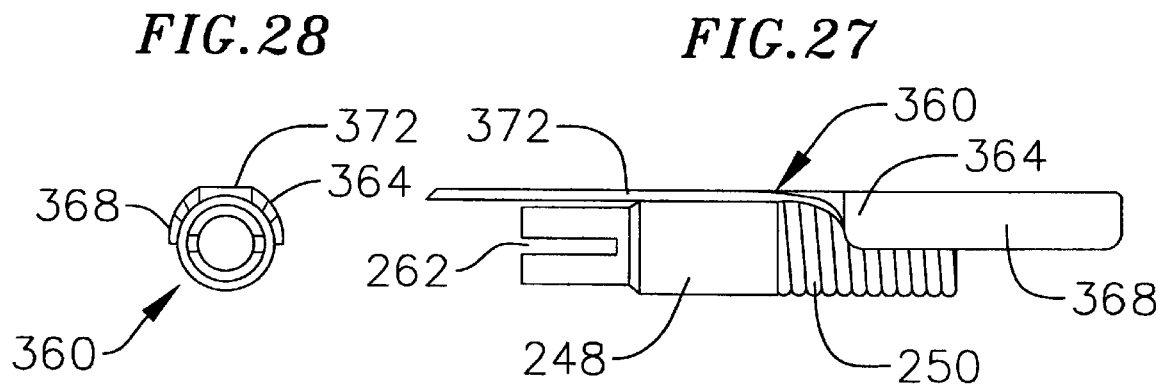
FIG. 27 is a side elevation view of the stiffener member illustrated in FIG. 25.
FIG. 28 is an end elevation view of the stiffener member illustrated in FIG. 25.

To provide still improved torque transfer utilizing the exemplary center support 330 illustrated in FIG. 22, the ribbed sleeve 302 illustrated in FIG. 19 may be utilized. Thus, as illustrated in FIG. 24, the lateral extensions 334 of the center support 330, when disposed within the inwardly projecting ribs 306 of the sleeve 302, provide a mechanical interference that assures good torque transfer. As with previous embodiments, adhesive material 280 is injected into the sleeve 302 during assembly of the device.

Figure 29:
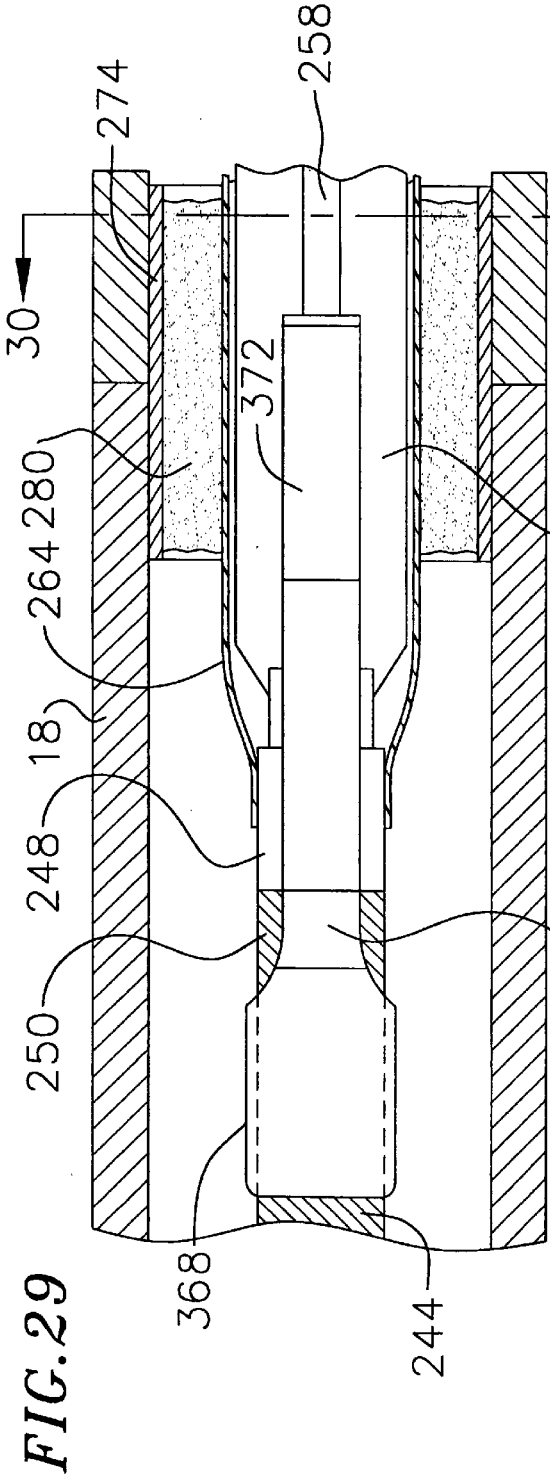
FIG. 29 is a side elevation view, having cut away portions, of a catheter including the stiffener member illustrated in FIG. 25.
Figure 30:
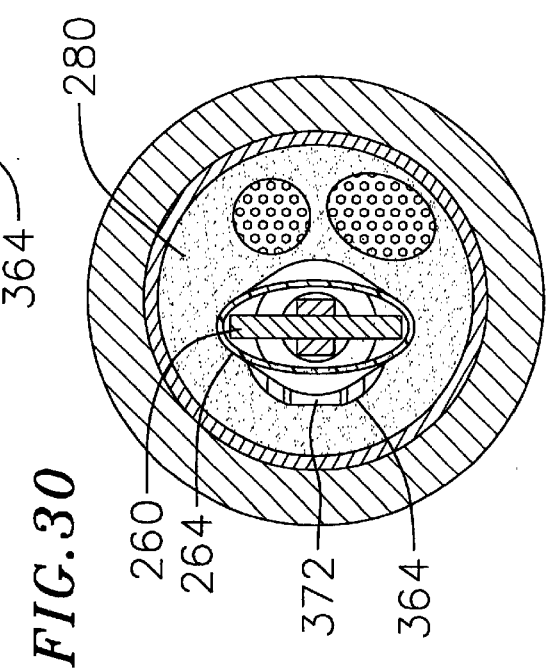
FIG. 30 is a section view taken along lines 30—30 in FIG. 29.

In accordance with another preferred embodiment, and as illustrated for example in FIGS. 25–28, an exemplary torque transfer device 360 includes a stiffener member 364 that is fixedly engaged by, for example, soldering, spot welding or adhesive, to the distal end 250 of the guide coil 244. The stiffener 364 member has a rounded proximal portion 368 to facilitate its engagement with the guide coil 244, and a longitudinally projecting distal end portion 372. As illustrated in FIGS. 29 and 30 the end portion 372 projects distally alongside of the steering sleeve 264 which encloses the steering center support 260 into the butt bond sleeve 274 (or the area of another type of bond). Thereafter, when adhesive material 280 is injected into the area where the proximal and distal catheter body members are secured to one another, the distal end 372 of the stiffener component 364 will be adhesively bonded therein. As a result, torque forces from the main body tube 18 are transferred through the adhesive material to the distal end 372 of the stiffener member 364. In the illustrated embodiment, the torque is therefore transferred through the stiffener member 364 to the steering guide coil 244, through the ferrule 248 to the steering center support 260, and thus to the catheter distal end assembly 22.

Figure 31:
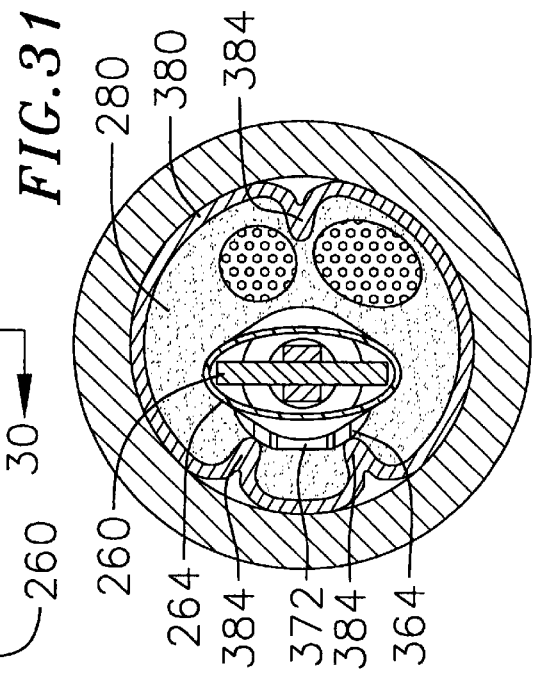
FIG. 31 is a section view of a catheter including a ribbed sleeve and the stiffener member illustrated in FIG. 25.

A further improvement in the torque transfer is achieved through the use of the stiffener 364 in combination with a ribbed sleeve that is similar to the sleeve 302 illustrated in FIG. 19. Specifically, as illustrated in FIG. 31, the distal end 372 of the stiffener 364 will project between the inwardly projecting ribs 384 of a three ribbed sleeve 380 to provide a mechanical interference that will provide torque transfer in addition to the torque transfer through the adhesive material 280.

Turning to FIG. 32, an exemplary sleeve 390 that can be utilized with the stiffener 364 (in a butt bond arrangement as well as other types of bonding arrangements) includes an extended rib-like portion having an inwardly projecting side wall 394 that forms an exterior channel 396. As illustrated in FIG. 33, the channel 396 is disposed such that the distal end 372 of the stiffener 364 resides within the channel 396. Alternatively, as illustrated in FIG. 34, a sleeve 398 having a gap or slot 399 in its sidewall which matingly engages the distal end 372 of the stiffener 364 can also be advantageously utilized where the diameter of the sleeve 390 is closer to the diameter of the guide coil 244.

IV. Alternative Bond Configurations

One preferred implementation of the present bond (or joint) configurations is in a steerable catheter, i.e. a catheter that includes a mechanism that allows the distal end to be manipulated from the proximal end. Typically, and as illustrated above, the steering mechanism includes a steering center support within the catheter body that is connected to one or more steering wires. Other types of steerable catheters simply include steering wires that are connected to an internal component near the distal portion of the catheter body or to the distal tip itself. It should be noted, however, that the present bond configurations are not limited to steerable catheters and may be employed in any and all types of catheters.

Figure 35:
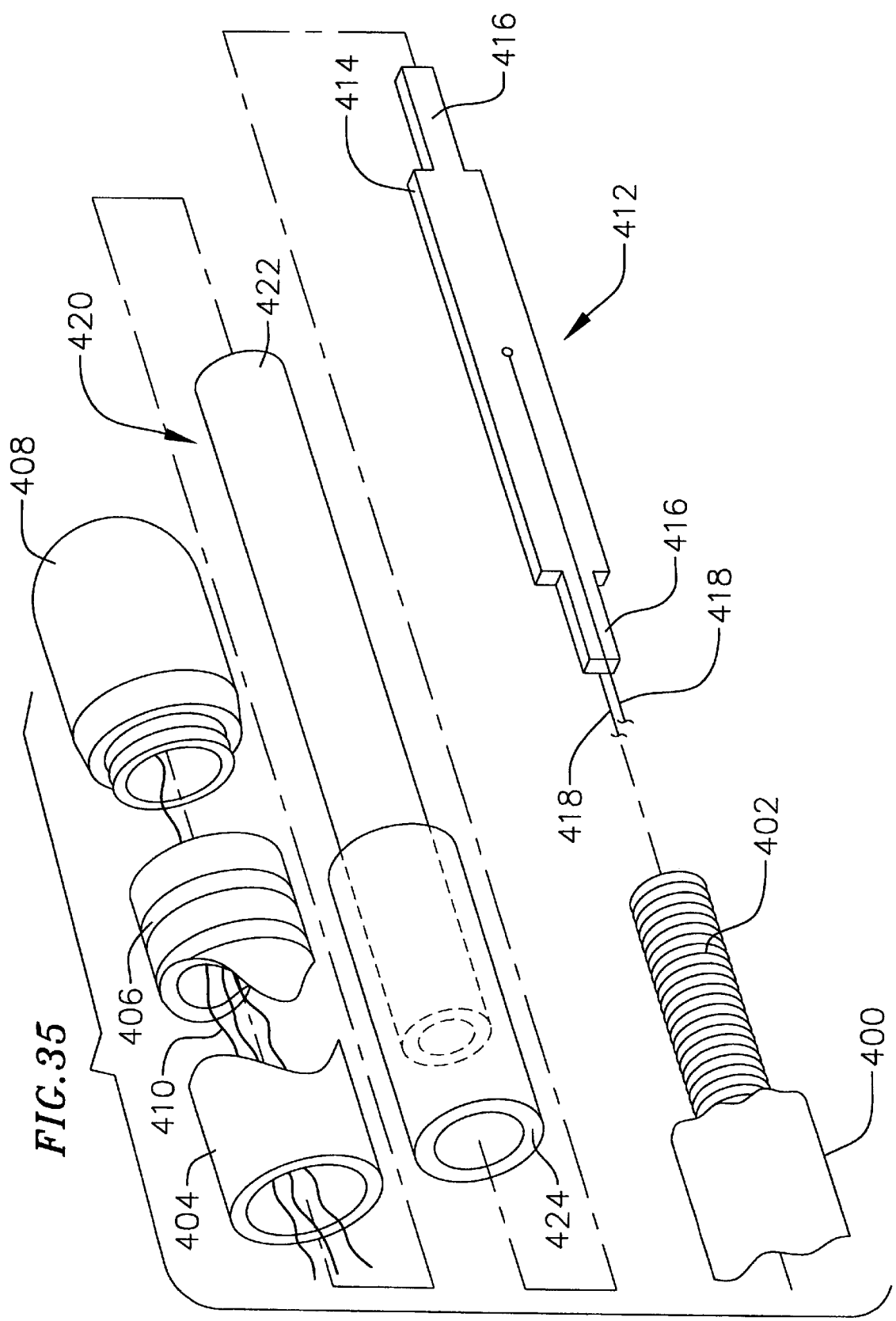
FIG. 35 is an exploded view in accordance with another preferred embodiment of a present invention.

As shown by way of example in FIG. 35, the present invention may be embodied in a catheter including a proximal member 400, an elongate guide coil 402, and a distal member 404. The proximal member 400 is preferably a braided plastic tube formed from Pebax®, or any other biocompatible thermoplastic. The elongate guide coil 402 extends to a point located proximal to the distal portion of the proximal member 400 and is preferably formed from stainless steel. The distal member 404, which is preferably a plastic tube formed from Pebax® or any other biocompatible thermoplastic, supports the electrodes 406 and tip electrode 408. A series of conducting wires 410, which run along the space between the guide coil 402 and the inner surface of the catheter, are connected to the electrodes 406 and 408 and to an electrical connector (not shown) that connects the catheter to an energy supply and control device. The conducting wires 410 transmit electrical current from the electrodes 406 that is indicative of activity within the heart, and transmit radio frequency energy to one or more of the electrodes 406 and 408 to perform soft tissue coagulation procedures. The conducting wires 410 also transmit signals from temperature sensors (not shown) that may be associated with one or more of the electrodes.

The exemplary embodiment also includes a distal steering assembly 412 that consists primarily of a bendable steering center support 414. The steering center support 414 is preferably about 0.035 inch wide, 0.005 inch thick, and 2 to 6 inches long and is formed from stainless steel. Of course, center supports formed from other materials and having different dimensions may also be used. In order to increase the stiffness of the center support 414, optional leaf springs may also be provided on one or both sides of the center support. The center support 414 includes a pair of shoulders 416. One of the shoulders is inserted into the guide coil 402 and the other is secured to the tip electrode 408. Preferably, the shoulder 416 is soldered to the tip electrode 408, thereby creating a rigid connection between the center support 414 and the tip electrode.

Steering wires 418 are secured to opposing sides of the steering center support 414. The steering wires 418 extend through the guide coil 402 and are connected to a control knob on the catheter handle. Rotation of the control knob causes the center support 414 and, therefore, the distal portion of the catheter, to deflect. Additional details concerning steering assemblies may be found in U.S. Pat. No. 5,257,451, which is incorporated herein by reference.

As illustrated, for example, in FIGS. 35 and 36, a sleeve assembly 420 covers the steering assembly 412 and a portion of the guide coil 402. The exemplary sleeve assembly 420 is a two-part assembly including a Teflon sleeve 422 that is reinforced with Kevlar and a polyester tube 424. Of course, the sleeve assembly is not limited to the exemplary two-part assembly and other materials having similar properties may be used. The Teflon sleeve 422 is secured to the guide coil 402 and steering center support 414 by heat shrinking it thereover. The Teflon sleeve 422 is also treated with either sandpaper or sand blasting to make its outer surface rough, thereby preventing rotation of the various components relative to one another during the assembly process. Prior to heat shrinking the polyester tube 424 over the Teflon sleeve 422, adhesive material is inserted therebetween. Once the adhesive material sets and the heat shrink process is complete, a substantially unitary structure including the sleeve assembly 420, center support 414 and tip electrode 408 (soldered to the center support) will remain.

The proximal member 400 and distal member 404 are arranged such that one overlaps the other. In the preferred embodiment illustrated in FIG. 36, the proximal member 400 overlaps the distal member 404, thereby creating an overlapping zone 426. The proximal and distal members are then secured to one another at the overlapping zone 426, preferably by a thermal bonding process. Alternatively, adhesive bonding may be used.

The proximal member 400 also includes a side wall aperture 428 near the distal end thereof. Preferably, the side wall aperture 428 is just proximal to the overlapping zone 426 and aligned with the sleeve assembly 420. In the preferred embodiment, the side wall aperture 428 has a diameter of about 0.023 inch. The side wall aperture 428 allows adhesive material 430 to be introduced into the catheter by, for example, an injection process employing a syringe-type dispenser that dispenses a preselected amount of the adhesive material. A preferred volume is approximately 50 micro liters. This will result in a layer of adhesive material 430 that extends around the periphery of the sleeve assembly 420 and is about 0.04 inch to about 0.06 inch in length. With respect to the adhesive material itself, a preferred adhesive material is cyanoacrylate adhesive sold under the trade name Loctite 4013. Of course, other suitable adhesive materials may also be used.

The adhesive material 430 connects the distal end of the proximal member 400 to the steering center support 414. Although this connection takes place by way of the sleeve assembly 420, the present invention is not so limited, especially when the invention is embodied in a non-steerable catheter. The connection advantageously provides a high fidelity torque transmission path from the proximal member 400 to the tip electrode 408. The side wall aperture 428 should be located close to the overlapping zone so that the torque transmitting capabilities of the proximal member 400 can be utilized as much as possible.

The catheter should be deflected a few times prior to the introduction of the adhesive material 430 in order to put some slack into the conducting wires 410. The slack is needed because the conducting wires 410 are located outside the guide coil 402 and sleeve assembly 420 and, therefore, will be fixed in place by the adhesive material 430. Without the slack, there would be at least some likelihood that the conducting wires 410 will separate from the electrodes and/or temperature sensors when the distal portion of the catheter is deflected. Other strain relief techniques may also be employed. Exemplary techniques include lightly tacking down the wires in place with an excess length of wire in the distal section, making a helical wind of wire in the distal section, threading the wires through a thin walled tube (such as a polyimide tube) that is longer than the adhesive bond section, and encasing the wires in an elastomeric coating. The steering wires 418, on the other hand, are located within the guide coil 402 and sleeve assembly 420 and are not effected by the adhesive material 430.

Subsequent to the introduction of the adhesive material 430, the side wall aperture 428 may be potted (or plugged) with adhesive material 431 to seal the catheter, as illustrated for example in FIG. 36A. UV adhesive is preferable because it is clean, cures fast and is flexible. The flexibility allows the UV adhesive to flex with the catheter and maintain the seal at the side wall aperture 428. The adhesive material 431 used to seal the side wall aperture 428 should also be the same color as the proximal member for aesthetic reasons.

It should be noted that any of the steering devices described in Section II above and any of the torque transfer devices described in Section III above may be used in conjunction with a catheter having the features described in this section.

In accordance with another preferred implementation of the present invention, the adhesive material can be introduced into the region of the catheter just proximal to the overlapping zone without the use of the side wall aperture 428. Specifically, prior to bonding the proximal and distal members 400 and 404 to one another at the overlapping zone 426, the distal member may be pulled away from the proximal member, thereby creating a small gap through which a needle can be inserted. The needle may be used to inject the adhesive material 430 into the space between the proximal member 400 and the sleeve assembly 420. Once the injection process has been completed, the proximal and distal members may be returned to an overlapping state and bonded to one another, either thermally or through the use of adhesive material.

Although the present invention has been described in terms of the preferred embodiment above, numerous modifications and/or additions to the above-described preferred embodiments would be readily apparent to one skilled in the art. By way of example, but not limitation, distal tip steering mechanisms other than the exemplary leaf-type steering center support arrangement may be employed. Additionally, the guide coil may be replaced by a guide tube, or simply eliminated. It is intended that the scope of the present invention extends to all such modifications and/or additions.

We claim:

1. A catheter, comprising:
   a hollow flexible catheter body defining a flexible proximal portion and a flexible distal portion;
   at least one internal component within the catheter body;
   a torque transfer device, defining an inner region and an exterior surface, located within the catheter body about the at least one internal component; and
   adhesive material located within the catheter body about the torque transfer device and within the inner region of the torque transfer device about the at least one internal component.

2. A catheter as claimed in claim 1, wherein the catheter body comprises a proximal member and a distal member secured to one another.

3. A catheter as claimed in claim 2, wherein the proximal member and distal member are secured to one another in a butt bond arrangement where the proximal and distal members abut one another.

4. A catheter as claimed in claim 3, further comprising:
   a butt bond sleeve having a portion located within and bonded to the proximal member and a portion located within and bonded to the distal member, at least a portion of the adhesive material being located within the butt bond sleeve.

5. A catheter as claimed in claim 4, wherein the torque transfer device is located within the butt bond sleeve.

6. A catheter as claimed in claim 4, wherein the torque transfer device comprises at least one rib projecting inwardly from the butt bond sleeve.

7. A catheter as claimed in claim 2, wherein the proximal member and distal member define respective proximal and distal portions and one of the proximal member distal portion and the distal member proximal portion overlaps the other, thereby defining an overlapping region.

8. A catheter as claimed in claim 7, wherein the proximal and distal members are thermally bonded at the overlapping region.

9. A catheter as claimed in claim 7, wherein the torque transfer device is located within the overlapping region.

10. A catheter as claimed in claim 1, further comprising:
    a handle connected to the proximal portion of the catheter body.

11. A catheter as claimed in claim 1, wherein the at least one internal component comprises a steering center support having at least one steering wire connected thereto.

12. A catheter as claimed in claim 11, wherein the steering center support includes a relatively wide proximal portion, a tapered central portion and a relatively narrow distal portion.

13. A catheter as claimed in claim 1, wherein the torque transfer device comprises a crimp sleeve disposed substantially around at least a portion of the at least one internal component and in contact with the adhesive material.

14. A catheter as claimed in claim 13, wherein the crimp sleeve comprises a tubular sleeve.

15. A catheter as claimed in claim 13, wherein the crimp sleeve comprises a substantially U-shaped sleeve.

16. A catheter as claimed in claim 13, wherein the crimp sleeve comprises a substantially C-shaped sleeve.

17. A catheter as claimed in claim 13, wherein the crimp sleeve comprises a substantially G-shaped sleeve.

18. A catheter as claimed in claim 1, wherein the torque transfer device comprises a stiffener member being fixedly engaged to the at least one internal component and in contact with the adhesive material.

19. A catheter as claimed in claim 18, wherein the stiffener member comprises a generally flat member having a curved portion that is engaged to the at least one internal component and a distally projecting arm portion that projects into the adhesive material.

20. A catheter as claimed in claim 1, wherein the torque transfer device comprises a laterally extending portion of the at least one internal component, the laterally extending portion being disposed within the adhesive material.

21. A catheter as claimed in claim 20, wherein the at least one internal component comprises a steering center support having at least one steering wire connected thereto.

22. A catheter as claimed in claim 1, wherein the torque transfer comprises a sleeve having at least one inwardly extending rib member located in the distal portion of the catheter body.

23. A catheter as claimed in claim 2, wherein the proximal member defines a proximal member stiffness, the distal member defines a distal member stiffness and the proximal member stiffness is greater than the distal member stiffness.

24. A catheter body as claimed in claim 23, wherein at least a portion of the adhesive material is located within the proximal member.

25. A catheter as claimed in claim 23, wherein the distal member defines a distal end, the catheter further comprising:
    a tip electrode secured to the distal end of the distal member.

26. A catheter as claimed in claim 23, further comprising:
    a plurality of spaced electrodes carried by the distal member.

27. A catheter as claimed in claim 23, wherein the distal member defines a distal end, the catheter further comprising:
    a tip member secured to the distal end of the distal portion.

28. A catheter as claimed in claim 1, wherein the distal portion of the catheter body defines a distal end, the catheter further comprising:
    a tip electrode secured to the distal end of the distal portion.

29. A catheter as claimed in claim 1, wherein the distal portion of the catheter body defines a distal end, the catheter further comprising:
    a tip member secured to the distal end of the distal portion.

30. A steering mechanism for use with a catheter, comprising:
    a steering center support defining a distal end and including a relatively wide proximal portion, a tapered central portion and a relatively narrow distal portion; and
    at least one steering wire secured to the relatively narrow distal portion of the center support a sufficient distance from the distal end of the center support to provide a straight distal end when the steering wire is activated to bend the center support.

31. A steering mechanism as claimed in claim 24, wherein the steering wire is connected to the center support at a point located approximately one inch from the distal end of the center support.

32. A catheter, comprising:
    a hollow flexible catheter body including a flexible proximal member defining proximal member stiffness and a flexible distal member defining a distal member stiffness secured to the proximal member, the proximal member stiffness being greater than the distal member stiffness;
    at least one internal component within the catheter body;
    a torque transfer device, defining an inner region and an exterior surface, located within the catheter body about the at least one internal component; and
    adhesive material located within the catheter body about the torque transfer device and within the inner region of the torque transfer device about the at least one internal component.

33. A catheter as claimed in claim 32, wherein the proximal member and distal member are secured to one another in a butt bond arrangement where the proximal and distal members abut one another.

34. A catheter as claimed in claim 33, further comprising:
    a butt bond sleeve having a portion located within and bonded to the proximal member and a portion located within and bonded to the distal member, at least a portion of the adhesive material being located within the butt bond sleeve.

35. A catheter as claimed in claim 34, wherein the torque transfer device is located within the butt bond sleeve.

36. A catheter as claimed in claim 32, wherein the distal member defines a distal end, the catheter further comprising:
    a tip electrode secured to the distal end of the distal member.

37. A catheter as claimed in claim 32, further comprising:
    a plurality of spaced electrodes carried by the distal member.

38. A catheter as claimed in claim 32, wherein the distal member defines a distal end, the catheter further comprising:
    a tip member secured to the distal end of the distal member.

39. A catheter as claimed in claim 32, wherein at least some of the adhesive is located within the proximal member.

40. A catheter, comprising:
    a hollow flexible catheter body;
    a guide coil within the catheter body;
    an internal component within the catheter body having a relatively flat region distal of the guide coil;
    a torque transfer device within the catheter body positioned about at least a portion of the relatively flat region of the internal component; and
    adhesive material within the catheter body coextensive with the relatively flat region of the internal component.

41. A catheter as claimed in claim 40, wherein the adhesive material is located between the torque transfer device and the catheter body.

42. A catheter as claimed in claim 41, wherein the adhesive material is located within between the torque transfer device and relatively flat region of the internal component.

43. A catheter as claimed in claim 40, wherein the toque transfer device is non-circular in cross-section.

44. A catheter as claimed in claim 43, wherein the toque transfer device is formed from metal.

* * * * *

UNITED STATES PATENT AND TRADEMARK OFFICE
CERTIFICATE OF CORRECTION

PATENT NO. : 6,287,301 B1
DATED : September 11, 2001
INVENTOR(S) : Russell B. Thompson et al.

It is certified that error appears in the above-identified patent and that said Letters Patent is hereby corrected as shown below:

<u>Title page,</u>
Item [56], after "5,964,757 10/1999 Ponzi." insert
-- 5,984,907 * 11/1999 McGee et al.. --

Signed and Sealed this

Twenty-second Day of October, 2002

Attest:

JAMES E. ROGAN
Attesting Officer *Director of the United States Patent and Trademark Office*